United States Patent [19]

Ushizawa et al.

[11] Patent Number: 4,816,394

[45] Date of Patent: Mar. 28, 1989

[54] QUANTITATIVE ANALYSIS OF 3α-HYDROXYSTEROID AND REAGENT USEFUL THEREFOR

[75] Inventors: Koji Ushizawa; Akemichi Maki; Toshiyuki Akimoto; Senkichi Nagasaki; Miyoshi Hirata, all of Tokyo, Japan

[73] Assignee: Daiichi Pure Chemicals Co., Ltd., Tokyo, Japan

[21] Appl. No.: 861,725

[22] Filed: May 12, 1986

[51] Int. Cl.$^4$ ............................................. C12Q 1/32
[52] U.S. Cl. ........................................ 435/26; 435/25
[58] Field of Search .......................................... 435/26

[56] References Cited

FOREIGN PATENT DOCUMENTS 0037742 10/1981 European Pat. Off. .
0054689 6/1982 European Pat. Off. .

OTHER PUBLICATIONS

Papanastasiou–Diamandi–Chem. Abst., vol. 101 (1984) p. 106700x.
Papanastasiou–Diamandi–Chem. Abst., vol. 99 (1983) p. 209041c.
"Comprehensive Biochemistry", vol. 13, 3rd Edition, pp. 80, 81, edited by M. Florkin et al., Elsevier Scientific Publishing Co., Amsterdam, NL; *p. 8, lines 6–11; p. 81, lines 13–18.
Fresenius Zeitschrift für Analytische Chemie, vol. 290, 1978, pp. 181, 182, Springer-Verlag, Berlin, DE; C. C. Gillhuus-Moe et al.: "Methodological Studies on a Direct Enzymatic Fluorometric Quantitation of Total Bile Acids in Serum".

*Primary Examiner*—Sam Rosen
*Attorney, Agent, or Firm*—Oblon, Fisher, Spivak, McClelland & Maier

[57] ABSTRACT

A 3α-hydroxysteroid contained in a sample can be quantitatively analyzed by causing a 3α-hydroxysteroid dehydrogenase to act on the sample in the presence of nicotinamide adenine dinucleotide, causing tetrazolium or a salt thereof, an electron carrier substance, and 3-oxosteroid-$\Delta^1$-dihydrogenase and/or 3-oxosteroid-$\Delta^4$-dehydrogenase to act on the thus-obtained reaction product, and then quantitatively analyzing the resultant formazan.

9 Claims, 1 Drawing Sheet

F I G. 1
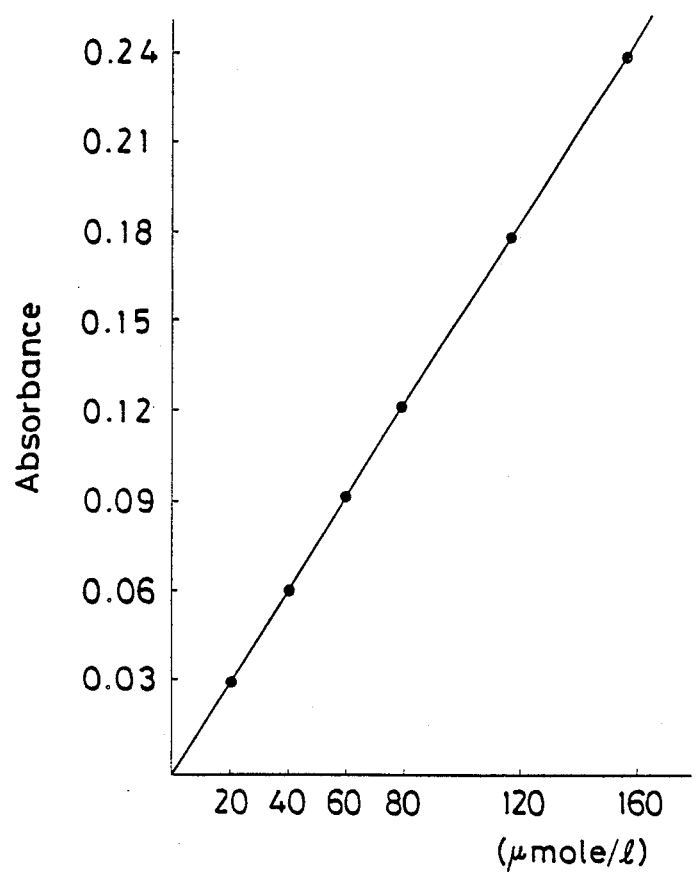

4,816,394

QUANTITATIVE ANALYSIS OF 3α-HYDROXYSTEROID AND REAGENT USEFUL THEREFOR

BACKGROUND OF THE INVENTION

1. Field of the Invention

This invention relates to a quantitative analysis of a 3α-hydroxysteroid, which makes use of the coupled enzyme method.

2. Description of the Prior Art

Among 3α-hydroxysteroids in an organism, there are steroid hormones such as androsterone, besides bile acid and the like. Of these, bile acid has particularly important significance for clinical diagnoses. Bile acid is composed principally of glucocholic acid, taurocholic acid, glucochenodeoxycholic acid, taurochenodeoxycholic acid, glucodoxycholic acid, taurodeoxycholic acid and the like. After having been synthesized from cholesterol in a liver, it is circulated through an extremely closed cycle called "enterohepatic circulation system". Bile acid is therefore contained only in a very trace amount in peripheral blood of healthy people. This cycle is however subjected to rhexis by a liver or biliary tract disease, resulting in an increased blood level of bile acid. Making use of such an increase in the blood level of bile acid as an index, it is therefore possible to diagnose such a liver or biliary tract disease and at the same time, to determine its graveness to a certain extent. For these reasons, it has become important to quantitatively analyze bile acid, which is one of 3α-hydroxysteroids, in an organism, especially, serum for the diagnosis of liver and/or biliary tract diseases.

As quantitative analyses of 3α-hydroxysteroids known to date, there are chromatography, enzyme assay, immunoassay, etc. In the field of routine clinical tests, enzyme assay is primarily used owing to its simplicity. Namely, 3α-hydroxysteroid dehydrogenase (hereinafter abbreviated as "3α-HSD") is caused to act on bile acid (a 3α-hydroxysteroid) in the presence of nicotinamide adenine dinucleotide (hereinafter abbreviated as "NAD"), thereby converting NAD to reduced nicotinamide adenine dinucleotide (hereinafter abbreviated as "NADH"). Thereafter, its quantitative analysis is carried out by any one of the following methods:

(1) The fluorescence of the resultant NADH is measured.

(2) The resultant NADH is converted back to NAD under the action of diaphorase and at the same time, coexisting resazurin is converted to resorufine. The fluorescence of the resorufine is then measured.

(3) The resultant NADH is converted back to NAD under the action of diaphorase and at the same time, coexisting nitroblue tetrazolium is converted to diformazan. The fluorescence of the diformazan is then subjected to colorimetry.

The above methods (1) and (2) are however fluorometric methods, and their procedures are complex and moreover they require expensive equipment. Under the circumstances, they are seldom relied upon in routine tests. On the other hand, the method (3) is poor in sensitivity. Moreover, it requires each sample in a large volume since the blood level of bile acid is extremely low. It is also prone to interference by other components in the sample. The method (3) is not therefore fully satisfactory.

SUMMARY OF THE INVENTION

An object of this invention is to develop an advantageous quantitative analysis for 3α-hydroxysteroids by making use of the enzyme method.

The present inventors have proceeded with an investigation of coupling reaction systems utilized in the enzyme method and their reaction products. The investigation led to an enzymatic coupling system which can oxidize a 3-oxosteroid, an oxidation product of a 3α-hydroxysteroid, further by 3-oxosteroid-$\Delta^4$(or $\Delta^1$)-dehydrogenase. It has thus been found that use of the enzymatic coupling system can provide a high-sensitivity quantitative analysis, resulting in completion of this invention.

In one aspect of this invention, there is thus provided a quantitative analysis of a 3α-hydroxysteroid contained in a sample, which comprises causing 3α-hydroxysteroid dehydrogenase to act on the sample in the presence of nicotinamide adenine dinucleotide, causing tetrazolium or a salt thereof, an electron carrier substance, and 3-oxosteroid-$\Delta^1$-dehydrogenase and/or 3-oxosteroid-$\Delta^4$-dehydrogenase to act on the thus-obtained reaction product, and then quantitatively analyzing the resultant formazan.

In another aspect of this invention, there is also provided a reagent useful for the quantitative analysis of a 3α-hydroxysteroid, which comprises nicotinamide adenine dinucleotide, 3α-hydroxysteroid dehydrogenase, tetrazolium or a salt thereof, an electron carrier substance, and 3-oxosteroid-$\Delta^1$-dehydrogenase and/or 3-oxosteroid-$\Delta^4$-dehydrogenase.

The term "formazan" as used herein is a collective or generic term for compounds containing a skeleton, $H_2NH=CHN=NH$. They may be formed, for example, by reduction of tetrazolium as in the quantitative analysis of this invention.

The quantitative analysis of this invention makes use of both formazan (1) from a conventionally-used enzymatic coupling system and formazan (2) from the enzymatic coupling system revealed by the present inventors. Accordingly, the quantitative analysis of this invention does not require procedures such as heat treatment of each sample, removal of proteins, extraction and the like and in addition, has such good sensitivity that it requires each serum or plasma sample in an amount as little as 50 μl or so in contrast to 100–1,000 μl in conventional methods.

The above and other objects, features and advantages of the present invention will become apparent from the following description and appended claims, taken in conjunction with the accompanying drawing.

BRIEF DESCRIPTION OF THE DRAWING

In the accompanying sole drawing:

FIG. 1 is a diagram showing the calibration curve obtained in Example 1. Absorbance is plotted along the axis of ordinates, while the concentration of added GC (μmole/l) is plotted along the axis of abscissas.

DETAILED DESCRIPTION OF THE INVENTION AND PREFERRED EMBODIMENTS

The reaction mechanism of the quantitative analysis of the present invention may be summarized as shown by the following reaction scheme.

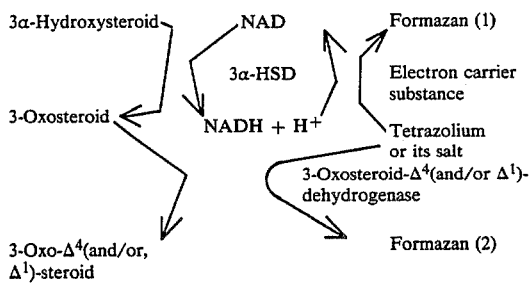

Namely, the quantitative analysis of this invention makes use of the conventionally known reaction, in which NADH is converted to NAD, and in addition, another reaction in which a 3-oxosteroid is converted to its corresponding 3-oxo-$\Delta^4$(and/or $\Delta^1$)-steroid, whereby formazan is formed from tetrazolium or its salt. The formazan is then subjected to a conventional quantitative analysis to determine the quantity of the 'α-hydroxysteroid.

For the practice of the quantitative analysis of this invention, the above-described reactions may be effected by adding, in an arbitrary order, a sample as well as NAD, tetrazolium or a salt thereof, an electron carrier substance, 3α-HSD, and either one or both of 3-oxosteroid-$\Delta^4$-dehydrogenase and 3-oxo-steroid-$\Delta^1$-dehydrogenase in a buffer. As a reagent useful in the practice of the quantitative analysis, may be used that obtained in advance by adding NAD, tetrazolium or a salt thereof, an electron carrier substance, 3α-HSD, and either one or both of 3-oxosteroid-$\Delta^4$-dehydrogenase and 3-oxosteroid-$\Delta^1$-dehydrogenase in a buffer. Alternatively, it is also possible to add, in advance, the above-mentioned components other than the enzyme or enzymes, NAD, or tetrazolium or its salt in a buffer and then to incorporate the thus-omitted component upon use of the reagent.

Any conventional buffers may be used in the quantitative analysis of this invention, such as phosphate buffers, Tris buffers and Good's buffers the pHs of which range from 6 to 10.

As salts of tetrazolium, may be employed nitroblue tetrazolium (hereinafter abbreviated as "NTB"), 3-(p-indophenyl)-2-(p-nitrophenyl)-5-phenyl-2H-tetrazolium chloride (hereinafter abbreviated as "INT"), 3-(4,5-dimethyl-2-thiazolyl)-2,5-diphenyl-2H-tetrazolium bromide (hereinafter abbreviated as "MTT"), 1,1'-(3,3'-dimethoxy-4,4'-bihphenylene)-bis(5-(4-nitrophenyl)-3-[4-(2-hydroxy-3-(2-hydroxyethyldiethylamino)propoxy)phenyl]}-2Htetrazolium chloride (hereinafter abbreviated as "W.S.NTB"), etc. The concentration of tetrazolum or its salt may be in a range of 50–2,000 μmole/l, preferably, 100–500 μmole/l.

NAD may be used at a concentration of 50–2,000 μmole/l, preferably, 100–500 μmole/l.

On the other hand, the concentration of 3α-HSD is sufficient so long as it falls within a range of 10–5,000 units/l. It is however preferred to use it in a range of 200–500 units/l.

As exemplary electron carrier substances, may be mentioned diaphorase, 1-methoxy-5-methylphenazinium methylsulfate (hereinafter abbreviated as "1-methoxy-PMS"), phenazine methosulfate (hereinafter abbreviated as "PMS"), 9-dimethylaminobenzo-α-phenazonium chloride (hereinafter abbreviated as "meldola blue"), and so on. As to their concentration ranges, 10–5,000 units/l or preferably 200–500 units/l may be mentioned for diaphorase, and 0.1–1,000 μ/mole/l or preferably 1–200 μmole/l may be recommended for the other electron carrier substances.

Furthermore, 3-oxosteroid-$\Delta^4$-dehydrogenase (EC.1.3.99.5,EC.1.3.99.6) or 3-oxosteroid-$\Delta^1$-dehydrogenase (EC.1.3.99.4) useful in the practice of this invention is widely found in microorganisms such as those belonging to the genus Pseudomonas [J. Chem. Soc.; Chem. Comm. 3, 115 (1974); J. Biol. Chem. 218, 675 (1956), ibid. 234, 2014 (1959); Biochem. Biophs. Acta 56, 584 (1962)], the genus of Arthrobactor [Eur. J. Biochem. 47, 555 (1974)]; the genus of Norcardia [Chemical and Pharmaceutical Bulletin 21, 2794 (1973), ibid. 23, 2164 (1975); Dissertatin Abstracts 35, 3839 (1975)]; the genus of Corynebacterium (U.S. Pat. No. 3,639,212), etc.

The present inventors cultured *Pseudomonas testosteroni* in accordance with the procedure proposed by Levy et al. in the above-mentioned "J. Biol. Chem." 234, 2014 (1959). From its cells, 3-oxosteroid-$\Delta^4$-dehydrogenase and 3-oxosteroid-$\Delta^1$-dehydrogenase were isolated for use in the present invention. In the present invention, it is sufficient to use them at a concentration in a range of 50–10,000 units/l with 300–3,000 units/l being particularly preferred.

The quantitative analysis of this invention can be applied to samples each of which contains one or more 3α-hydroxysteroids. Illustrative of such samples may be serum, plasma, urine, etc.

The quantitative analysis of a 3α-hydroxysteroid by this invention may be carried out in the following manner. After conducting the reaction in the above-described manner, a terminating solution is added to the reaction mixture to terminate the reaction and the absorbance of formazan is then determined. Alternatively, the increase of the formazan in a prescribed period of time in the reaction mixture may be measured in terms of absorbance. As the terminating solution, it is possible to use an inorganic acid such as hydrochloric acid, sulfuric acid or phosphoric acid or an organic acid such as citric acid or acetic acid.

In the quantitative analysis of this invention, formazan (1) and formazan (2) are formed as shown by the above-described reaction mechanism and their absorbance levels are then measured. Since the quantitative analysis of this invention is carried out on both formazans (1) and (2), it permits high-sensitivity measurements.

Having generally described this invention, a further understanding can be obtained by reference to certain specific examples which are provided herein for purpose of illustration only and are not intended to be limiting unless otherwise specified.

EXAMPLE 1

Samples (50 μl, each) were separately added to 0.5 ml of a 50 mmol/l phosphate buffer (pH 7) containing 400 μmol/l of NAD, 200 μmol/l of NBT, 500 units/l of diaphorase, 200 units/l of 3α-HSD and 500 units/l of 3-oxosteroid-$\Delta^4$-dehydrogenase (hereinafter called "measuring reagent"). They were reacted at 37° C. for 10 minutes precisely. Thereafter, 0.5 ml of a reaction terminating solution (0.1N HCl) was added. After allowing the reaction mixtures to stand for 5 minutes, their absorbance levels were measured at a wavelength of 540 nm. The above procedure was repeated on the same samples using the same measuring reagent except for the omission of 3α-HSD to use the results as a sample blank (blank test). As the samples, serum added with glucocholic acid (hereinafter abbreviated as "GC") was diluted to various concentrations by additive-free serum. Results are shown in Table 1. A calibration curve obtained on the basis of the results is shown in FIG. 1.

TABLE 1

| Concentration of added GC (μmole/l) | 20 | 40 | 60 |
|---|---|---|---|
| Absorbance | 0.030 | 0.061 | 0.092 |
| Concentration of added GC (μmole/l) | 80 | 120 | 160 |
| Absorbance | 0.122 | 0.177 | 0.238 |

EXAMPLE 2

Ten serum samples, each of 50 μl, were used and the procedure of Example 1 L was repeated to determine the absorbance levels of the respective serum samples. From the regression equation of the resultant calibration curve ($y = 1.474x + 2.118$, y: m-Abs, x: μmole/l), the amount of 3α-hydroxysteroid was calculated. Results are shown in Table 2.

TABLE 2

| Sample No. | Absorbance (Abs) | Amount of 3α-hydroxysteroid (μmole/l) |
|---|---|---|
| 1 | 0.010 | 5.3 |
| 2 | 0.015 | 8.7 |
| 3 | 0.014 | 8.1 |
| 4 | 0.038 | 24.3 |
| 5 | 0.014 | 8.1 |
| 6 | 0.011 | 6.0 |
| 7 | 0.047 | 30.4 |
| 8 | 0.073 | 48.1 |
| 9 | 0.043 | 27.7 |
| 10 | 0.083 | 54.9 |

EXAMPLE 3

The procedure of Example 1 was repeated except that the measuring reagent was added with 500 units/l of 3-oxosteroid-Δ$^1$-dehydrogenase, thereby obtaining a calibration curve.

TABLE 3

| Concentration of added GC (μmole/l) | 20 | 40 | 60 |
|---|---|---|---|
| Absorbance | 0.058 | 0.114 | 0.176 |
| Concentration of added GC (μmole/l) | 80 | 120 | 160 |
| Absorbance | 0.229 | 0.337 | 0.452 |

EXAMPLE 4

The procedure of Example 1 was repeated except that 150 μmol/l of 1-methoxy-PMS was used in lieu of diaphorase in the measuring reagent, thereby obtaining a calibration curve.

TABLE 4

| Concentration of added GC (μmole/l) | 20 | 40 | 60 |
|---|---|---|---|
| Absorbance | 0.026 | 0.052 | 0.075 |
| Concentration of added GC (μmole/l) | 80 | 20 | 160 |
| Absorbance | 0.102 | 0.150 | 0.199 |

EXAMPLE 5

Samples (50 μl, each) were separately added to 0.5 ml of a 50 mmol/l Tris hydrochloride buffer (pH 9.0) containing 400 μmol/l of NAD, 200 μmol/l of W.S.NTB, 500 units/l of diaphorase, 200 units/l of 3α-HSD and 500 units/l of 3-oxosteroid-Δ$^4$-dehydrogenase (hereinafter called "measuring reagent"). They were reacted at 37° C. for 10 minutes precisely. Thereafter, 0.5 ml of the reaction terminating solution (0.1N HCl) was added. After allowing the reaction mixtures to stand for 5 minutes, their absorbance levels were measured at a wavelength of 600 nm. The above procedure was also repeated on the same samples using the same measuring reagent except for the omission of 3α-HSD to use results as a sample blank (blank test). As the samples, serum added with GC was diluted to various concentrations by additive-free serum. A calibration curve was obtained.

TABLE 5

| Concentration of added GC (μmole/l) | 20 | 40 | 60 |
|---|---|---|---|
| Absorbance | 0.013 | 0.037 | 0.052 |
| Concentration of added GC (μmole/l) | 80 | 120 | 160 |
| Absorbance | 0.074 | 0.103 | 0.135 |

EXAMPLE 6

The procedure of Example 1 was repeated except that 200 μmol/l of NTB and 25 μmol/l of meldola blue were used instead of W.S.NTB and diaphorase in the measuring reagent, thereby obtaining a calibration curve.

TABLE 6

| Concentration of added GC (μmole/l) | 20 | 40 | 60 |
|---|---|---|---|
| Absorbance | 0.030 | 0.063 | 0.090 |
| Concentration of added GC (μmole/l) | 80 | 120 | 160 |
| Absorbance | 0.116 | 0.165 | 0.218 |

Having now fully described the invention, it will be apparent to one of ordinary skill in the art that many changes and modifications can be made thereto without departing from the spirit or scope of the invention as set forth herein.

What is claimed as new and is secured by Letters Patent is:

1. A method of quantitatively analyzing for a 3α-hydroxysteroid in a sample, comprising:
   (a) reacting 3α-hydroxysteroid dehydrogenase with said sample in the presence of nicotinamide adenine dinucleotide;
   (b) allowing a combination of a tetrazolium compound or salt thereof, an electron carrier substance and 3-oxosteroid-Δ$^1$-dehydrogenase and/or 3-oxosteroid-Δ$^4$-dehydrogenase to react with the 3-oxosteroid compound obtained by oxidation of said 3α-hydroxysteroid in said sample in step (a); and
   (c) quantitatively analyzing for the formazan product which results from the reaction of step (b).

2. The method of claim 1, wherein said electron carrier substance is diaphorase, 1-methoxy-5-methylphenazinium methylsulfate or 9-dimethylaminobenzo-α-phenazoxonium chloride.

3. The method of claim 1, wherein the concentration of nicotinamide adenine dinucleotide in the reaction medium of step (a) ranges from 50–2,000 μmole/l.

4. The method of claim 1, wherein the concentration of said 3α-hydroxysteroid dehydrogenase in the reaction medium of (a) is within the range of 10–5,000 units/l.

5. The method of claim 1, wherein the concentration of said tetrazolium compound or salt thereof in the reaction medium of step (b) ranges from 50–2,000 μmole/l.

6. The method of claim 1, wherein the concentration of said electron carrier substance in step (b) ranges from 10–5,000 units/l.

7. A reagent useful for the quantitative analysis of a 3α-hydroxysteroid, comprising: nicotinamide adenine dinucleotide, 3α-hydroxysteroid dehydrogenase, a tetrazoium compound or a salt thereof, an electron carrier substance and 3-oxosteroid-$\Delta^1$-dehydrogenase and/or 3-oxosteroid-$\Delta^4$-dehydrogenase.

8. The reagent of claim 7, wherein said electron carrier substance is diaphorase, 1-methoxy-5-methylphenazinium methylsulfate or 9-dimethylaminobenzo-α-phenazoxonium chloride.

9. The reagent of claim 7, wherein said tetrazolium compound is nitroblue tetrazolium, 3-(p-indophenyl)-2-(p-nitrophenyl)-5-phenyl-2H-tetrazolium chloride, 3-(4,5-dimethyl-2,2-thiazolyl)-2,5-diphenyl-2H-tetrazolium bromide or 1,1'-(3,3'-dimethoxy-4,4'-biphenylene)-bis[5-(4-nitrophenyl)-3-[4-(2-hydroxy-3-(2-hydroxyethyldiethylamino)propoxy)phenyl]]-2H-tetrazolium chloride.

* * * * *

UNITED STATES PATENT AND TRADEMARK OFFICE
Certificate

Patent No. 4,816,394                                                                          Patented: Aug. 30, 1988

On petition requesting issuance of a certificate for correction of inventorship pursuant to 35 U.S.C. 256, it has been found that the above-identified patent, through error and without any deceptive intent, improperly sets forth the inventorship.

Accordingly, it is hereby certified that the correct inventorship of this patent is: Koji Ushizawa, Akemichi Maki, Toshiyuki Akimoto, Senkichi Nagasaki, Miyoshi Hirata and Takae Shigihara, all of Tokyo Japan.

Signed and Sealed this 16th Day of April, 1991.

ROBERT A. WAX

*Supervisory Patent Examiner*
*Art Unit 187*